United States Patent [19]
Gipson, II

[11] Patent Number: 6,099,813
[45] Date of Patent: Aug. 8, 2000

[54] TOOTHBRUSH HOLDER AND SANITIZER CASE

[76] Inventor: Lovelace Preston Gipson, II, 1040 Twinkletown Rd., Memphis, Tenn. 38116

[21] Appl. No.: 09/108,050

[22] Filed: Jun. 30, 1998

[51] Int. Cl.[7] .................................................. A61L 2/18
[52] U.S. Cl. ..................... 422/300; 422/297; 422/292; 206/209.1; 132/308; 132/315; D6/528; D6/534
[58] Field of Search ............... 422/28, 292, 297, 422/300; 206/209, 209.1, 210, 581, 365, 369, 63.5, 823, 362.2, 15.2; 132/308, 315; D6/528, 534

[56] References Cited

U.S. PATENT DOCUMENTS

| | | | |
|---|---|---|---|
| 1,451,425 | 4/1923 | Hurley | 406/209.1 |
| 3,207,296 | 9/1965 | Goodall | 206/209.1 |
| 3,342,544 | 9/1967 | Curiel | 422/300 |
| 3,741,378 | 6/1973 | Parker | 206/209.1 |
| 4,884,688 | 12/1989 | Hurst | 422/300 |
| 4,997,629 | 3/1991 | Marchand et al. | 422/300 |

*Primary Examiner*—Robert J. Warden, Sr.
*Assistant Examiner*—Fariborz Moazzam
*Attorney, Agent, or Firm*—John J. Mulrooney

[57] ABSTRACT

A toothbrush case is a unitary receptacle having a bristle chamber and a handle chamber separated by a fluid seal. The case opens for insertion and removal of the toothbrush and closes to form a sealed container where the brushes and handle are stored in separate, fluid-impervious, sanitizing environments. The case has ports with uni-directional flow valves through which sterilizing agents in the form of aerosol spray or fluid may be selectively admitted into the brush compartment or the handle compartment. Upon application of the sterilizing agent, the toothbrush is sterilized and maintained in a sterile environment until the case is opened for use.

9 Claims, 1 Drawing Sheet

TOOTHBRUSH HOLDER AND SANITIZER CASE

BACKGROUND OF THE INVENTION

1. Field of the Invention

This invention relates to a container for receiving and sterilizing a toothbrush, and storing it in a sanitary environment between uses.

2. Description of the Prior Art

The prior art generally recognizes that bacteria, germs and other debris collect on toothbrushes and are introduced into the mouth when the toothbrush is used, and that health professionals recommend changing toothbrushes frequently to insure proper oral hygiene and the overall health of toothbrush users. See U.S. Pat. No. 4,997,629 to Marchand and U.S. Pat. No. 4,915,219 to Ottimo. These prior patents also recognize the economic benefit of sterilizing brushes between uses as an alternative to discarding brushes before their useful life is past.

Toothbrush sterilization containers are generally known in the art. U.S. Pat. No. 1,194,540 to Quartararo discloses a toothbrush case in which the bristles are positioned above a pad saturated with a volatile sterilizing fluid which evaporates to provide fumes that permeate and sterilize the bristles.

U.S. Pat. No. 1,200,236 to Ray discloses a toothbrush holder in the form of a tubular container which may be opened to insert and immerse the bristles in a germicidal solution and the open end of the tube may be closed and sealed to prevent leakage.

U.S. Pat. No. 3,207,296 to Goodall discloses a container which encloses the entire toothbrush in a sterilizing environment created by the evaporation or sublimation of a germicidal pellet to form air currents to which the bristles are exposed.

U.S. Pat. No. 4,884,688 to Hurst discloses a toothbrush case having a reservoir with an opening therein through which a sterilizing solution or mouthwash solution is poured into the reservoir for cleaning or sterilization of the toothbrush.

The fact that these prior toothbrush holders are not in widespread use indicates that such holders are deficient in some way or unacceptable to toothbrush users for some reason. A problem with toothbrush holders which rely upon germicidal fumes to sterilize, e.g., U.S. Pat. Nos. 1,194,540 and 3,207,296, is that circulating fumes are not effective in sterilizing the bristles. The prior devices which totally immerse the bristles in sterilizing solution use more solution than needed to sterilize the bristles and must carry an unnecessarily large supply of disinfecting solution in a form which is susceptible to spillage.

SUMMARY OF THE INVENTION

An object of the present invention is to provide a case adapted to hold a toothbrush when not in use, to keep the toothbrush clean, and simultaneously to sterilize the bristles so that, between each successive use thereof, the brush is thoroughly sterilized to insure proper oral hygiene and avoid disease and infection.

Another object of the present invention is to provide a unitary, fluid-tight travel case for holding a toothbrush in a clean and sterilizing environment.

Another object of the present invention is to provide a toothbrush travel case which avoids spillage of sterilizing solution by providing for admission of the solution to the case from an aerosol can or prepackaged bag of solution through a port having a unidirectional flow valve.

These and other objects of the invention are achieved in a toothbrush case consisting of a unitary receptacle having a bristle chamber and a handle chamber separated by a fluid seal. The case opens for insertion and removal of the toothbrush and closes to form a sealed container where the bristles and handle are stored in separate, isolated, chambers. The case has ports with uni-directional flow valves through which sterilizing agents from spill-proof containers such as aerosol cans or a prepackaged containers of sterilizing solution may be selectively admitted into the brush compartment or the handle compartment. Upon application of the sterilizing agent, the toothbrush is sterilized and maintained in a sterile environment until the case is opened for use.

DESCRIPTION OF THE PREFERRED EMBODIMENTS

Figure 1:
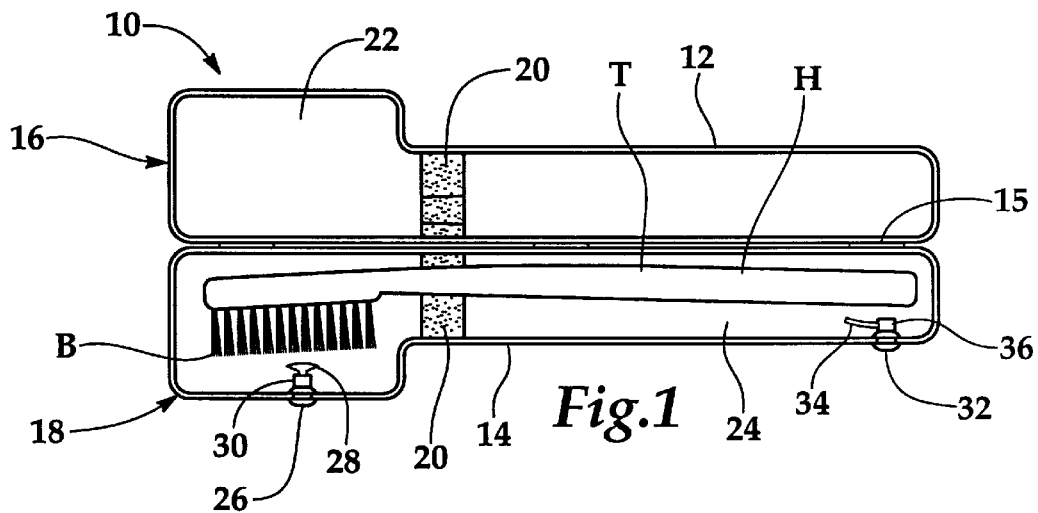
FIG. 1 is a top view of a preferred embodiment of a toothbrush case according to the present invention, with the case open and a toothbrush stored therein.
Figure 2:
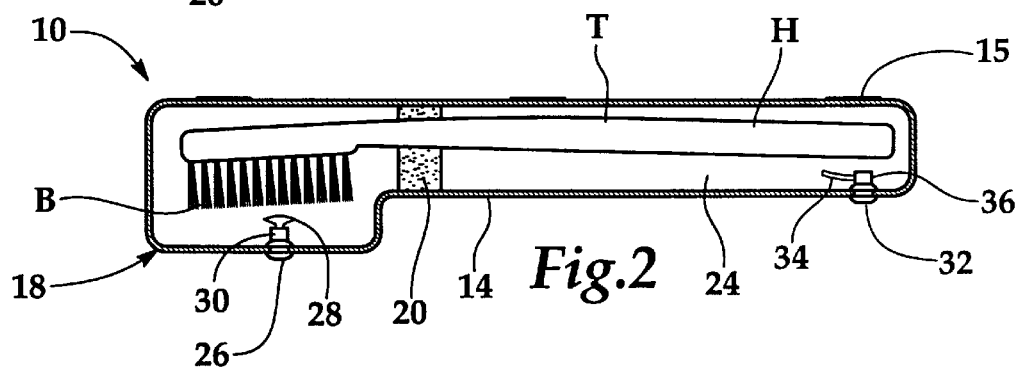
FIG. 2 is a side elevation view of the toothbrush case of the present invention, with the case closed and a toothbrush stored therein.

Referring to FIGS. 1 and 2, a toothbrush case 10 has mating sides or parts 12 and 14 in the general shape and length of a toothbrush. Sides 12 and 14 may be connected by hinge or other joining means 15 which permit the case to open in book-like fashion as shown in FIG. 1. Alternatively, sides 12 and 14 may be separable members. However, whether joined or separate, sides 12 and 14 are capable of mating, whereby they fit together to form a unitary, fluid-tight container capable of holding a toothbrush in a sanitizing environment. Case 10 is adapted to receive a toothbrush T having a handle H and bristles B. Case sides 12 and 14 have enlarged areas 16 and 18 at one end to accommodate the bristles B.

Case sides 12 and 14 each house part of a seal 20 which, when the sides are closed, forms a fluid-tight seal dividing the case 10 into a bristle chamber 22 and a handle chamber 24. When the case is closed by bringing sides 12 and 14 together in a mating fit as shown in FIG. 2, the seal 20 functions to isolate bristle chamber 22 from handle chamber 24. The seal 20 also functions to position, grip and hold toothbrush T in place within the case 10.

The case 10 has a first inlet port 26 connected to a tube 28 with a unidirectional flow valve 30 therein to provide a path for one-way fluid communication from outside to inside the sealed bristle chamber 22 as hereinafter described. The length and orientation of tube 28 within bristle chamber 22 is such that when a sterilizing fluid S is admitted through port 26 and tube 28, the fluid spray S is applied directly to bristles B of the toothbrush.

The case 10 has a second inlet port 32 connected to a tube 34 with a unidirectional flow valve 36 therein to provide a path for one-way fluid communication from outside to inside the sealed handle chamber 24. The length and orientation of tube 34 within handle chamber 22 is such that when a sterilizing fluid S is admitted through port 32 and tube 34, the fluid S is applied directly to handle H of the toothbrush.

Figure 3:
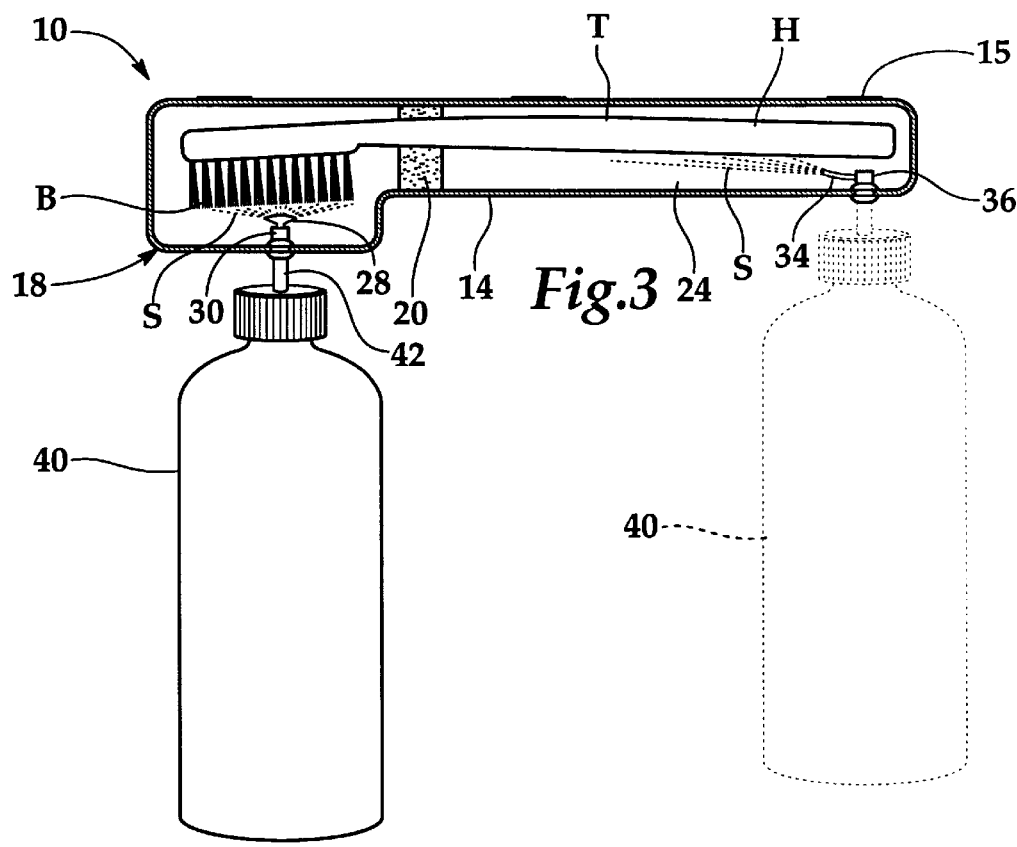
FIG. 3 is a side elevation view of the toothbrush case of the present invention showing an aerosol can connected in solid line format to deliver sterilizing solution to the bristle chamber of the case and in dotted line format to the handle chamber.

Referring to FIG. 3, the bristles B of a toothbrush stored in case 10 are sterilized by the introduction into bristle chamber 18 of a sterilizing agent through outlet spout 42 of a pressurized aerosol can 40 through inlet port 26. After introduction of a sterilizing agent into bristle chamber 22, the bristles B become and remain sterilized until the case is opened for use.

The toothbrush holder and sanitizer case described herein provides a useful and hygienic apparatus adapted to hold a toothbrush when not in use, to keep the toothbrush clean, and simultaneously to sterilize the bristles so that, between each successive use thereof, the brush is thoroughly sterilized to insure proper oral hygiene and avoid disease and infection. The case described herein also provides a fluid-tight toothbrush carrying case and avoids spillage and/or waste of disinfecting solutions by using aerosol cans and prepackaged bags of sterilizing solution.

It will be appreciated by those skilled in the art that changes could be made to the embodiments described above without departing from the inventive concept thereof. It is the intention of the inventor to cover by the appended claims all changes and modifications which are within the spirit and scope of the invention as defined by such claims.

I claim:

1. A case for holding and sterilizing a toothbrush comprising:
    a first side;
    a second side, said first and second sides being capable of a mating fit to form a fluid-tight container capable of holding a toothbrush;
    a fluid seal in said first and second sides, whereby, when said sides are mated, said case is divided into a first isolated chamber for receiving the toothbrush bristles and a second isolated chamber for receiving the toothbrush handle;
    a port in said case to permit fluid communication from outside said case into said isolated bristle chamber; and
    a uni-directional flow valve in said port to permit one-way fluid flow into said isolated bristle chamber.

2. A toothbrush case as claimed in claim 1 further comprising: a second inlet port having a uni-directional flow valve therein to permit one-way fluid communication from outside said case into said isolated handle chamber.

3. A toothbrush case as claimed in claim 1, wherein said inlet port is adapted to receive the outlet spout of a container of sterilizing solution.

4. A toothbrush case as claimed in claim 1, wherein said inlet port is adapted to receive the output spout of an aerosol container of pressurized sterilizing solution.

5. A toothbrush case as claimed in claim 1, wherein said first and second sides are connected by means permitting said sides to be separated to expose said toothbrush and closed to encase said toothbrush.

6. A case for holding and sterilizing a toothbrush comprising:
    a first side;
    a second side, said first and second sides being capable of a mating fit to form a fluid-tight container capable of holding a toothbrush;
    hinge means connecting said first and second sides, whereby said sides may be moved between open and closed positions;
    means in said case to divide said case into an isolated bristle chamber and an isolated handle chamber;
    a port in the case at said bristle chamber;
    a fluid conduit connected to said port; and
    a uni-directional flow valve in said fluid conduit for admitting sterilizing solution into said bristle chamber.

7. A toothbrush case as claimed in claim 6 further comprising: a second inlet port in the case at said handle chamber, said second inlet port having a uni-directional flow valve therein to permit one-way fluid communication from outside said case into said isolated handle chamber.

8. A toothbrush case as claimed in claim 6, wherein said inlet port is adapted to receive the outlet spout of a container of sterilizing solution.

9. A toothbrush case as claimed in claim 6, wherein said inlet port is adapted to receive the output spout of an aerosol container of pressurized sterilizing solution.

* * * * *